United States Patent [19]
Johnson

[11] Patent Number: 5,823,746
[45] Date of Patent: Oct. 20, 1998

[54] REUSABLE PRESSURE PLATES AND METHODS

[75] Inventor: Jay Gregory Johnson, Maple Plain, Minn.

[73] Assignee: SIMS Deltec, Inc., St. Paul, Minn.

[21] Appl. No.: 702,384

[22] Filed: Aug. 14, 1996

[51] Int. Cl.$^6$ .................................................. F04B 43/08
[52] U.S. Cl. ............................ 417/53; 417/474; 417/572
[58] Field of Search .................................. 417/53, 477.1, 417/477.2, 572, 474, 234, 360, 478, 479; 604/151, 153, 264, 280; 128/DIG. 12, DIG. 13; 137/343, 565

[56] References Cited

U.S. PATENT DOCUMENTS

| | | |
|---|---|---|
| 3,402,673 | 9/1968 | Ballentine et al. . |
| 3,559,644 | 2/1971 | Stoft et al. . |
| 3,620,650 | 11/1971 | Shaw . |
| 4,187,057 | 2/1980 | Xanthopoulos . |
| 4,236,880 | 12/1980 | Archibald . |
| 4,482,347 | 11/1984 | Borsanyi . |
| 4,559,038 | 12/1985 | Berg et al. . |
| 4,565,542 | 1/1986 | Berg . |
| 4,585,399 | 4/1986 | Baier . |
| 4,650,469 | 3/1987 | Berg et al. . |
| 4,657,486 | 4/1987 | Stempfle et al. . |
| 4,671,792 | 6/1987 | Borsanyi . |
| 5,017,059 | 5/1991 | Davis . |
| 5,074,756 | 12/1991 | Davis . |
| 5,078,683 | 1/1992 | Sancoff et al. . |
| 5,165,874 | 11/1992 | Sancoff et al. . |
| 5,213,483 | 5/1993 | Flaherty et al. . |
| 5,226,886 | 7/1993 | Skakoon et al. . |
| 5,336,190 | 8/1994 | Moss et al. . |
| 5,397,222 | 3/1995 | Moss et al. . |
| 5,425,173 | 6/1995 | Moss et al. . |
| 5,531,697 | 7/1996 | Olsen et al. . |
| 5,551,850 | 9/1996 | Williamson et al. ................... 417/474 |
| 5,564,915 | 10/1996 | Johnson . |
| 5,601,420 | 2/1997 | Warner et al. .......................... 417/474 |

FOREIGN PATENT DOCUMENTS

| | | |
|---|---|---|
| WO 93/10853 | 6/1993 | WIPO . |
| WO 96/27402 | 9/1996 | WIPO . |
| WO 97/02059 | 1/1997 | WIPO . |

OTHER PUBLICATIONS

Photographs of a pump product by Patient Solutions, Inc., Med–Mate™, Model 1100, pp. A1–A5.
Photographs of a pump product by Block Medical, Inc., a Hillenbrand Industry, Verifuse® Model No. B001500, pp. B1–B3.
Photographs of a pump product by Medfusion, Inc., a Medex, Inc. Company, Infu–Med™, WalkMed™ 440 PIC, pp. C1–C2.
Photographs of a pump product by C.R. Bard, Inc., Bard Medsystems Division, pp. D1–D3.
Photographs of a pump product by Pharmacia Deltec, Inc., pp. E1–E2.
Photographs of a pump product by AVI, Inc., AVI Guardian™ MICRO 110, pp. F1–F4.
Photographs of a pump product by Abbott Laboratories, Abbott/Shaw LifeCare®Pump Model 3, pp. G1–G3.
Patient Solutions, Inc. literature for MedMate™ 1100, 2 pages.
Patient Solutions, Inc. Directions for Use, MedMate™ model 1100, 61 pages.

(List continued on next page.)

*Primary Examiner*—Charles G. Freay
*Attorney, Agent, or Firm*—Merchant, Gould, Smith, Edell, Welter and Schmidt, P.A.

[57] ABSTRACT

This invention relates to reusable pressure plates designed to position tubing along a tubing support surface to facilitate peristaltic pumping of fluids from a fluid reservoir to a patient. Preferred embodiments of this invention include reinforced pump anchors to securably but releasably affix the pressure plate to the control module portion of an infusion system and cantilevered spring support to maintain pump accuracy and enabling the use of more durable materials for pressure plate manufacture.

9 Claims, 3 Drawing Sheets

OTHER PUBLICATIONS

Block Medical, Inc. literature for VERIFUSE System, 1 page, dated Nov. 1990.

Medfusion, Inc. Operations Manual for Medfusion WALK-MED™ Ambulatory Infusion Pump, 92 pages, dated Apr., 1990.

Medex Ambulatory Infusion Systems literature, entitled "WalkMed Pump Disposable Products," 2 pages, dated 1992.

Medex Ambulatory Infusion Systems literature, entitled "WalkMed PCA," 2 pages, dated 1993.

Bard Ambulatory PCA Pump literature, 2 pages, dated Jun. 1990.

Bard MedSystems Division, C.R. Bard, Inc., Quick Reference Guide, 2 pages, dated Feb. 1992.

Bard MedSystems Division, C.R. Bard, Inc., Bard® Ambulatory PCA Pump Operator's Manual, 43 pages, dated Apr. 1990.

AVI, Inc., literature entitled "The AVI Advantage," 2 pages, dated 1983.

AVI, Inc. literature, entitled "Bridging the Gap," 6 pages, dated Apr. 22, 1983.

Abbott Laboratories Hospital Products Division literature, entitled "The Blue Line System LifeCare®," 16 pages, dated Jul., 1990.

Abbott Laboratories Hospital Products Division literature, entitled "LifeCare® Electronic Flow Control Systems Catalog," 34 pages, dated May, 1985.

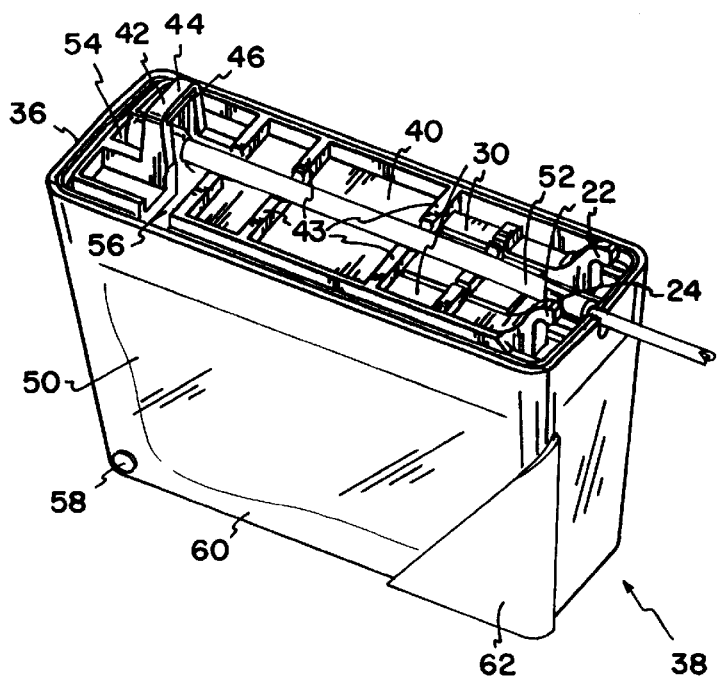
FIG. 2
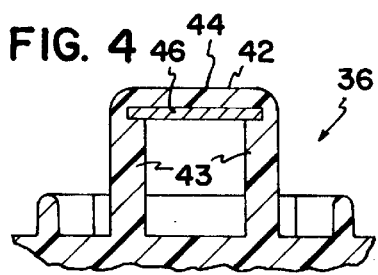
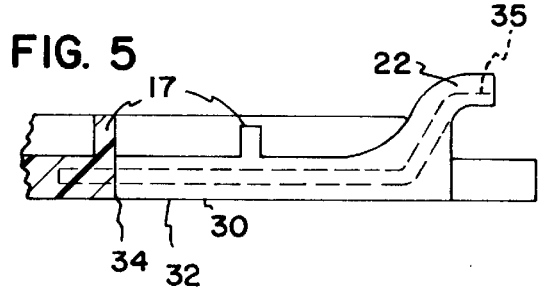
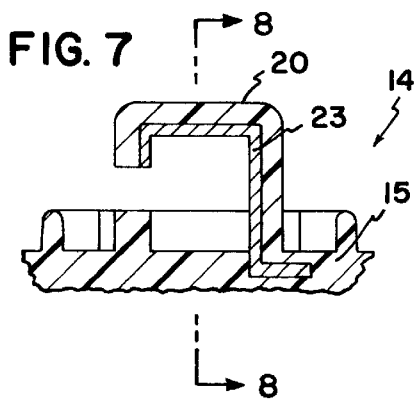
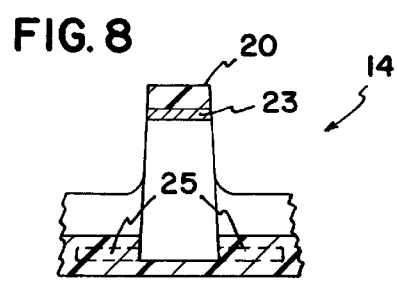

5,823,746

REUSABLE PRESSURE PLATES AND METHODS

FIELD OF THE INVENTION

The present invention relates to infusion systems and to ambulatory pumps for delivering fluid to a patient. In particular, this invention relates to reusable pressure plates and their methods for use.

BACKGROUND OF THE INVENTION

In medical applications, it is sometimes necessary to deliver fluid intravenously to a patient undergoing treatment. The fluid may be contained in a bag or other fluid reservoir, conveyed through a tube, and inserted into the patient's vein. At times, the amount of fluid conveyed to the patient must be controlled or regulated. In those instances where the fluid to the patient must be controlled, pumps have been used.

One pump is described in U.S. Pat. No. 4,559,038. This pump controls the delivery of fluid from the reservoir to the patient. In the '038 patent, the fluid is in a bag held in a container, or cassette, immediately adjacent to the pump. The pump controls the amount of fluid to the patient by physically pressuring the tube from the bag to the patient, and restricting the volume of fluid allowed to flow to the patient. The pump includes a pump mechanism which engages the tube and squeezes the tube against a pressure plate of the cassette to effect pumping of fluid.

It is also known to use the pump with a fluid reservoir that is remote, or separate from the pump. Typically, in a remote system, the fluid is contained in a bag and hung on a device separate from the pump. The bag has a tube extending from the bag, across a section of the pump, and then to the patient. Again, the pump controls the amount of fluid to the patient by mechanical pressure on the tube. A pressure plate mounted to the pump allows the pump mechanism to engage the tube to effect pumping.

In the past, certain types of pressure plates have been used to connect the pump to the tube. Because of reasons such as safety and cleanliness, the pressure plate is permanently attached to the tube. When the fluid reservoir is empty, or the treatment to the patient completed, the tube and pressure plate are thrown away. Disposing of the pressure plate contributes to waste and expense. There is a need for systems and methods that allow reuse of the pressure plate. Reuse of pressure plates raises concerns of patient safety as the pressure plates are reused over extended time periods. Fatigue and wear may alter pump performance if the pressure plate does not properly mount to the pump. Prior single use pressure plates were made of polycarbonate.

SUMMARY OF THE INVENTION

One aspect of the present invention relates to a reusable pressure plate mountable to a control module for positioning a tube adjacent to a plurality of tube engaging members of a pumping mechanism. The pressure plate includes a tubing support surface, and an anchor located on the tubing support surface for mounting the tubing support surface to the control module. The anchor includes a strengthening member. Two hooks are provided for mounting the tubing support surface to the control module. The two hooks can also be reinforced with strengthening members.

Another aspect of the present invention relates to a reusable pressure plate including a tubing support surface, a pump anchor for mounting the tubing support surface to the control module, and two hooks for mounting the tubing support surface to the control module, wherein the hooks each include a cantilevered spring member extending along the tubing support surface.

The present invention also relates to methods of reusing reinforced pressure plates and methods of reusing pressure plates including spring members configured to introduce predetermined flexibility into the pressure plate.

BRIEF DESCRIPTION OF THE DRAWINGS

FIG. 2 is a perspective view of a second embodiment showing a pressure plate with a cassette;

FIG. 4 is a cross-sectional end view of the reinforced anchor of the pressure plate of FIG. 2;

FIG. 5 is cross-sectional side view of the pump securing extension of the pressure plates of FIGS. 1 and 2;

FIG. 7 is a cross-sectional end view of the reinforced anchor of the pressure plate of FIG. 6;

FIG. 8 is a cross-sectional side view of the reinforced anchor of the pressure plate of FIG. 7 along lines 8—8;

DETAILED DESCRIPTION OF THE PREFERRED EMBODIMENTS

Figure 1:
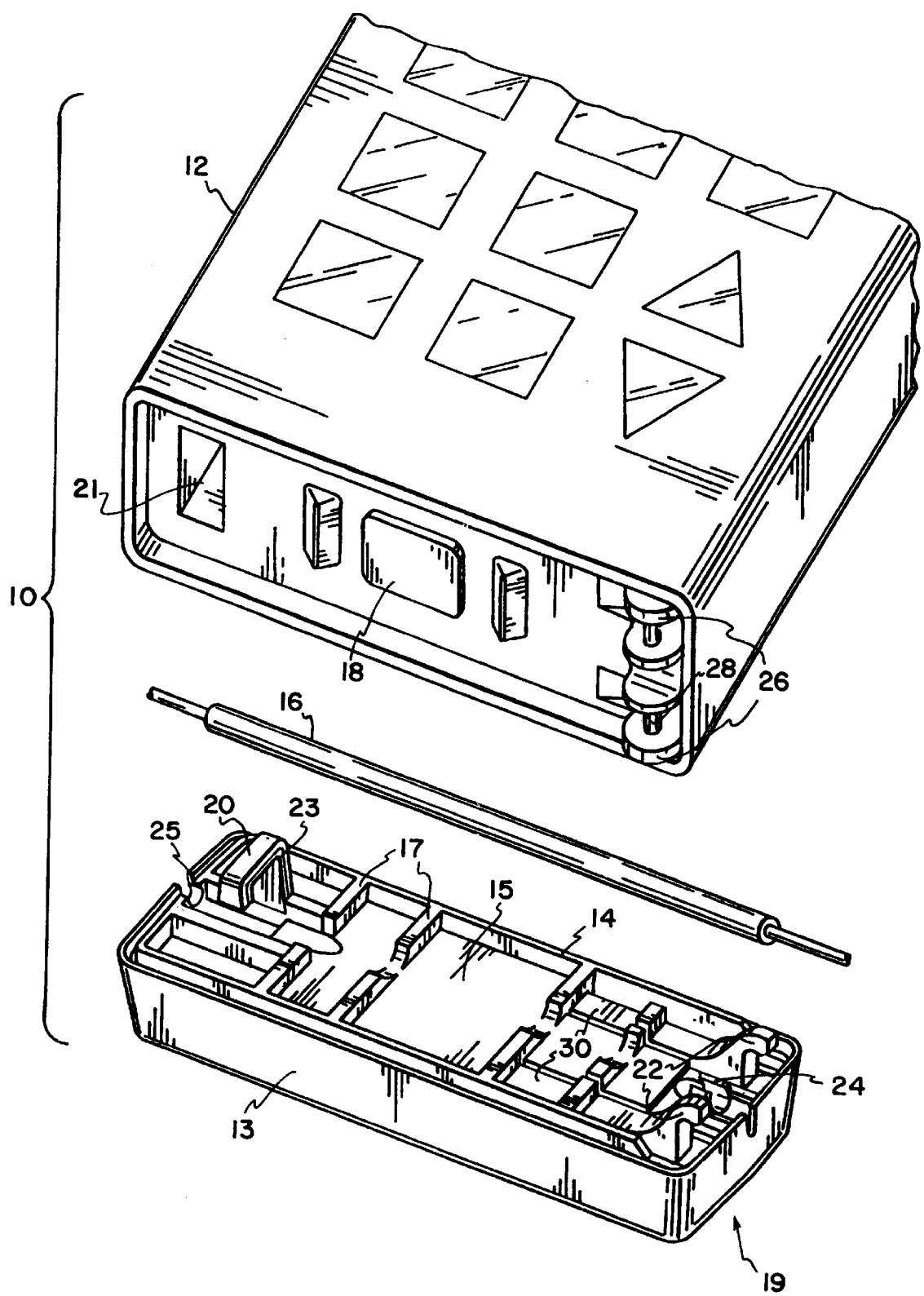
FIG. 1 is a perspective view of a first embodiment of this invention including a pressure plate in an infusion system using a pumping mechanism.
Figure 3:
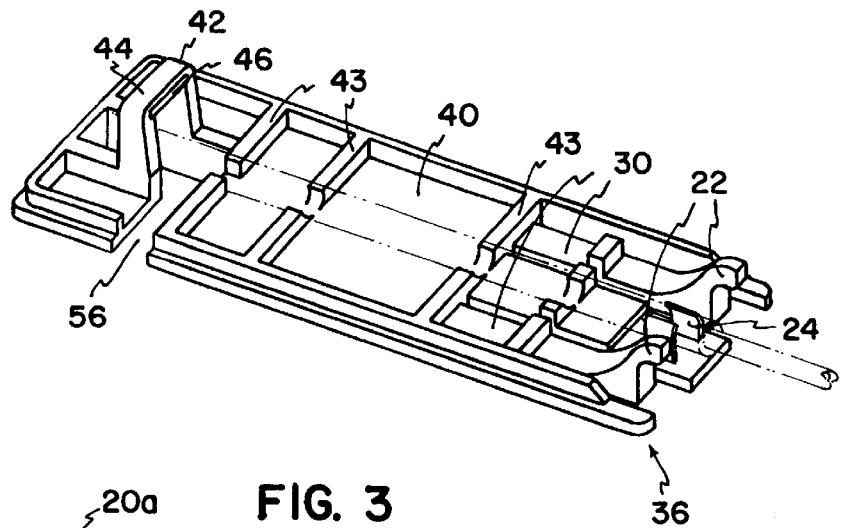
FIG. 3 is a perspective view of the pressure plate of FIG. 2.

This invention relates to reusable pressure plates suitable for supporting a tube extending from a fluid reservoir to a pump to deliver fluid to a patient. The tube is supported by the pressure plate adjacent to the tube engaging members of the pump. Pressure plates may wear or fail over time if reused with replacement tubes. In particular, the elements of the pressure plate that affix the pressure plate to the pump can wear or fail from fatigue after repeated use. This invention is directed to improving the useful life of the pressure plate so that wear and fatigue concerns are reduced or eliminated, while addressing the need for accurate delivery of fluid to the patient.

Reference will now be made in detail to the present preferred embodiments of the invention wherein like reference numerals indicate like elements through the several views. Referring now to FIGS. 1, and 5–8, an infusion pump 10 employs a linear peristaltic pumping mechanism. Infusion pump 10 of FIG. 1 includes a control module 12 and a pressure plate 14. Pressure plate 14 includes a tubing support surface 15 and a plurality of rib pairs 17 that serve as guides to position a tube 16 in place along tubing support surface 15. Tube 16 passes between control module 12 and pressure plate 14 guided by rib pairs 17 of tubing support surface 15 such that compressions from tube-engaging members 18 of control module 12 sequentially compress tube 16 against pressure plate 14 to direct fluid through tube 16 into the patient. Pressure plate 14 has a lower support or housing 13 which adds strength to pressure plate 14. Housing 13 can be a separate piece mounted to pressure plate 14, or integrally formed. Together, pressure plate 14 and housing 17 form a cassette 19 used with remote reservoirs. Pressure plate 14 could also be used with a housing enclosing a fluid reservoir, or no housing.

Pressure plate 14 is secured to control module 12 through the use of an anchor 20 and two pump securing extensions or hooks 22. Pump securing extensions 22 on tubing support surface 15 engage a suspended pin assembly having support structures 26 and pins 28 located on control module 12. Anchor 20 engages a releasable securing mechanism (latch) inside control module 12 within cavity 21. A lock can also be provided with control module 12 to prevent unauthorized unlatching.

Anchor 20 in the embodiment of FIGS. 1 and 6–8 is configured as a hook to facilitate the assembly and disassembly of the tube onto and off of the pressure plate. In these pump arrangements, tube 16 is positioned beneath anchor 20. One advantage of a hook-shaped anchor is the ease with which tube 16 can be assembled or removed from the tubing support surface 15 of pressure plate 14 in preparation for disassembly or reuse. Tube 16 does not have to be threaded through a small opening, such as would be the case if anchor 20 was closed. Any fittings or other elements on tube 16 do not interfere with anchor 20 during removal from or attachment to pressure plate 14. One disadvantage of hook-shaped anchors is that they may be a weaker structure as compared with a closed loop anchor like anchor 42 of the embodiment of FIG. 2. During use, anchor 20 is subjected to high loads. This is a particular concern where the pressure plate is subject to multiple use.

Anchor 20 receives significant stress when the pressure plate is repeatedly engaged and disengaged from the pump, as occurs during pressure plate reuse. As shown in FIGS. 1 and 6–8, anchor 20 includes a strengthening member such as an anchor reinforcement 23. Preferably, the anchor reinforcement is a more durable and stronger component than a remainder of the pressure plate. One preferred anchor reinforcement is made of metal. A remainder of pressure plate 14 can be made of molded plastic, such as polycarbonate. Anchor reinforcement 23 can be embedded during manufacture into the pressure plate tubing support surface 15. Anchor reinforcement addresses both fatigue and wear concerns for reuse of anchor 20. Anchor reinforcement 23 can be seen by cross-section in FIG. 7 embedded in pressure plate tubing support surface 15. FIG. 8 provides a second cross-section of anchor 20 with anchor reinforcement 23 taken along lines 8–8 as provided by the arrows of FIG. 7. FIG. 8 shows that reinforcement 23 embeds in tubing support surface 15 and extends within the tubing support surface 15 in two directions.

Figure 9:
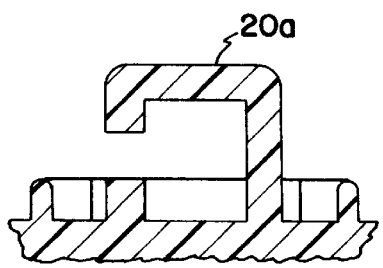
FIG. 9 is a cross-sectional end view of a portion of an alternative embodiment of a pressure plate with an open hook shape for the anchor and showing a single material construction.

Another technique for increasing the strength and durability of hook-shaped anchor 20 is to construct the entire pressure plate from a single durable material (see anchor 20a of FIG. 9). However, such a change in material may reduce the amount of flexibility in the pressure plate so as to create problems when the pressure plate is used with the pump. An all plastic (e.g., polycarbonate) construction includes a small amount of flexibility of the anchor, the securing extensions and the main body. The pressure plate is able to flex with the movement of tube engaging members 18 if necessary. This flexing allows the mechanical aspects of the control module that facilitate the peristaltic action to move without high current drains and/or stalling while at the same time not allowing free flow of fluid. If the pressure plate is too rigid, there is a concern that the tube engaging members may not be able to extend fully without interference from the pressure plate due to too tight a fit between the pressure plate and the control module, and there may occur pump stoppage or high energy drain. The pressure plates of this invention can be designed from durable materials to facilitate reuse including, but not limited to steel, aluminum, reinforced plastic (such as glass-filled polymers), and the like. The use of durable materials, such as metals, for a pressure plate reduces the risk of damage to the pressure plate through repeated use. The number of times that the pressure plate can be reused if made with these materials is increased as compared to pressure plates currently in use. However, these materials may not allow for sufficient flexibility during use.

Figure 6:
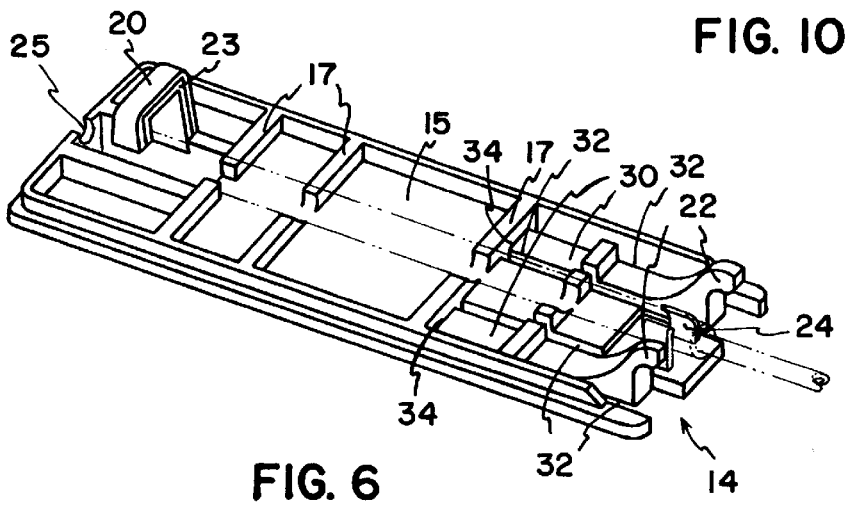
FIG. 6 is a perspective view of the pressure plate of FIG. 1.

As shown in FIGS. 1, 5 and 6, the pump securing extensions 22 employ cantilevered spring supports 30 that extend along the tubing support surface. Spring supports 30 are spaced from the rest of pressure plate 14 along side edges 32. Spring supports 30 are connected to the rest of pressure plate 14 at proximal ends 34. Spring supports 30 extending from pump securing extension 22 build back in the appropriate flexibility into the pressure plates prepared from more durable materials. For example, the use of the spring supports allows more durable materials to be used for pressure plate construction to permit reuse. Spring supports 30 with pump securing extensions 22 permit a more durable pressure plate to be coupled to existing control modules without creating pump stoppage problems or high energy drains.

The spring required to compensate for a change in the pressure plate material can be adjusted through the length and thickness of the spring support 30 on pump securing extensions 22. Thus, those skilled in the art of medical device design will be readily able to adjust the thickness and length of the spring supports 30, as needed, to maintain the accuracy of fluid delivery by the peristaltic pump function of the control module. Spring supports 30 and pump securing extensions 22 can also be reinforced with a strengthening member 35, as shown in FIG. 5. Strengthening member 35 is optional, but preferred if a remainder of pressure plate 14 is made of plastic (except for anchor reinforcement 23). Strengthening member 35 is not needed if entire pressure plate 14 is made from a more durable material such as metal and reinforced plastics.

Pressure plate 14 includes a first clip 24 and a second clip 25 at opposite ends of pressure plate 14 for releasably gripping tube 16 during use. Such a construction allows for convenient removal and replacement of a new tube.

Figure 10:
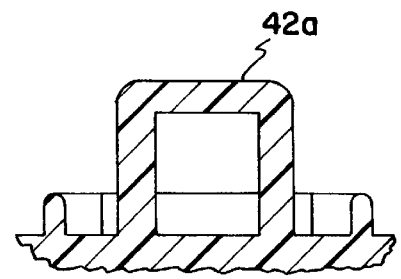
FIG. 10 is a cross-sectional end view of a portion of an alternative embodiment of a pressure plate with a closed loop shape for the anchor and showing a single material construction.

Referring now to FIGS. 2–5, an alternative pressure plate 36 is shown as part of a reusable cassette 38 which houses a fluid reservoir. Pressure plate 36 includes a tubing support surface 40, an anchor 42, rib pairs 43, and cantilevered spring supports 30 with extending pump securing extensions 22. Anchor 42 is prepared with sides 43 and top 44. Anchor 42 includes an anchor reinforcement 46 also seen in cross-section in FIG. 4. Reinforcement 46 configured as a small plate extends across the under surface of top 44 of anchor 42. Preferably, reinforcement 46 is prepared from a durable material such as steel, aluminum or another metal and a remainder of pressure plate 36 from a molded plastic, such as polycarbonate. Alternatively, the entire pressure plate can be made from a single durable material (see anchor 42a of FIG. 10).

The reusable cassette includes means for accessing the interior of the cassette to position a fluid reservoir 50 therein. A tube 52 extends from the fluid reservoir through port 54 positioned beneath anchor 42. In FIG. 2, cassette 38 includes a hinge 58 positioned at a first bottom corner of front face 60 of cassette 38. A positioning support 62 is positioned over a second bottom corner of front face 60. Front face 60 rotates upward in FIG. 2 about hinge 58 to provide access to the interior of the housing. A slot 56 formed in tubing support surface 40 communicates with port 54 and extends to the edge of tubing support surface 40 that communicates with front face 60. Slot 56 allows tube 52 attached to reservoir 50 to be removed from the tubing support surface 40. It will be appreciated that the reinforced anchors of this invention can be incorporated onto a variety of reusable cassette configurations where the cassette is mountable to an ambulatory infusion pump. Pressure plate 36 includes cantilevered spring supports 30, and tube clip 24 as noted above for pressure plate 14.

This invention also relates to methods for reusing pressure plates. In this method the pressure plate 14 is removed from the control module 12 (See FIG. 1) using the anchor releasing mechanism. The pressure plate is separated from pin assembly 24 on control module 12 and the tube 16 is removed from the pressure plate. A second tube is positioned beneath the pump anchor, along tubing support surface 15. The pressure plate is then repositioned on pin assembly 24 of the control module and the pump anchor is introduced into cavity 21 to engage the releasable securing mechanism within the control module 12. Since the pressure plates of this invention can be used with the control modules designed for prior art pressure plates, the reusable pressure plates of this invention can be substituted for other pressure plates without modification to the control module. Where the pressure plate is designed for use with a cassette housing a fluid reservoir, such as in FIG. 2, the cassette with the pressure plate is removed from the control module and the hinge is activated to provide access to the interior of the housing. The fluid reservoir and tubing are removed from the housing and a second reservoir with tubing is positioned in the housing with the tubing positioned along the tubing support surface.

Although characteristics and advantages, together with details for structure, materials, function and process steps, have been described in reference to preferred embodiments herein, it is understood that the disclosure is illustrative. To that degree, various changes made especially to matters of shape, size and arrangement to the full extent extended by the general meaning of the terms in which the appended claims are expressed, are within the principles of the present invention.

What is claimed is:

1. A pressure plate mountable to a control module for positioning a tubing adjacent to a plurality of tube engaging members of a pumping mechanism, the pressure plate comprising:
   a tubing support surface;
   an anchor for mounting the tubing support surface to the control module located on the tubing support surface, the anchor including a reinforcement; and
   two hooks for mounting the tubing support surface to the control module, wherein the hooks each include a cantilevered spring member extending along the tubing support surface.

2. The pressure plate of claim 1, wherein the anchor is closed loop-shaped.

3. The pressure plate of claim 1, wherein the anchor is hook-shaped.

4. A pressure plate mountable to a control module for positioning a tubing adjacent to a plurality of tube engaging members of a pumping mechanism, the pressure plate comprising:
   a tubing support surface;
   a pump anchor for mounting the tubing support surface to the control module located on the tubing support surface; and
   two hooks for mounting the tubing support surface to the control module, wherein the hooks each include a cantilevered spring member extending along the tubing support surface.

5. The pressure plate of claim 4, wherein the tubing support surface, the pump anchor, and the two hooks are made of metal.

6. The pressure plate of claim 4, wherein the two hooks each include a strengthening member.

7. A method for reusing a pressure plate mountable to a control module in an infusion system, the method comprising the steps of:
   disengaging a pressure plate having a tubing support surface and a reinforced pump anchor positioned on the tubing support surface from a control module;
   removing a first tube from the tubing support surface of the pressure plate;
   positioning a second tube along the tubing support surface of the pressure plate; and
   engaging the reinforced pump anchor with a releasable securing mechanism within the control module.

8. The method of claim 7, wherein the pressure plate further includes at least one cantilevered spring support.

9. A method for reusing a pressure plate mountable to a control module in an infusion system, the method comprising the steps of:
   disengaging a pressure plate having a tubing support surface and two cantilevered hooks positioned on the tubing support surface, the two cantilevered hooks having a portion extending parallel to and in the same plane as the tubing support surface;
   removing a first tube from the tubing support surface of the pressure plate;
   positioning a second tube along the tubing support surface of the pressure plate; and
   engaging the hooks with a pin assembly of the control module.

\* \* \* \* \*